United States Patent
Umbach

(10) Patent No.: US 10,016,295 B2
(45) Date of Patent: Jul. 10, 2018

(54) SAFE SLEEVE GASTRECTOMY

(71) Applicant: Thomas Umbach, Las Vegas, NV (US)

(72) Inventor: Thomas Umbach, Las Vegas, NV (US)

(*) Notice: Subject to any disclaimer, the term of this patent is extended or adjusted under 35 U.S.C. 154(b) by 143 days.

(21) Appl. No.: 15/269,578

(22) Filed: Sep. 19, 2016

(65) Prior Publication Data

US 2018/0078396 A1   Mar. 22, 2018

(51) Int. Cl.
*A61B 17/08* (2006.01)
*A61F 5/00* (2006.01)
*A61B 17/072* (2006.01)

(52) U.S. Cl.
CPC .......... *A61F 5/0083* (2013.01); *A61B 17/072* (2013.01); *A61F 5/0089* (2013.01)

(58) Field of Classification Search
CPC ..... A61F 5/0083; A61F 5/0086; A61B 17/072
See application file for complete search history.

(56) References Cited

FOREIGN PATENT DOCUMENTS

| RU | 2233625 | 8/2004 |
| RU | 2269948 | 2/2006 |
| RU | 2290893 | 1/2007 |

OTHER PUBLICATIONS

Gianos, Understanding the Mechanisms of Action of Sleeve Gastrectomy on Obesity, Third International Consensus Summit on Sleeve Gastrectomy, Bariatric Times, vol. 8, No. 5, May 2011, Supplement, p. 4, par. 1-5, last par.
Pryakhin, Surgical Treatment of Obesity, Longitudinal Resection of the Stomach, Department of Surgery, South Ural State Medical University of Minzdrav of Russia, 2015, p. 20, last par.

*Primary Examiner* — Melanie Tyson
(74) *Attorney, Agent, or Firm* — Lightbulb IP, LLC

(57) ABSTRACT

A safe sleeve gastrectomy reduces gastric volume of a patient's stomach as a weight loss treatment. The safe sleeve gastrectomy utilizes a safety pocket created by a surgeon to increase safety and guide division of the stomach. An instrument tunnel is created to facilitate division of the stomach into a pouch and a sectioned portion. In this manner, over or complete mobilization of the stomach is avoided. The sectioned portion may be lifted for increased visibility to facilitate its mobilization and removal from the patient.

20 Claims, 8 Drawing Sheets

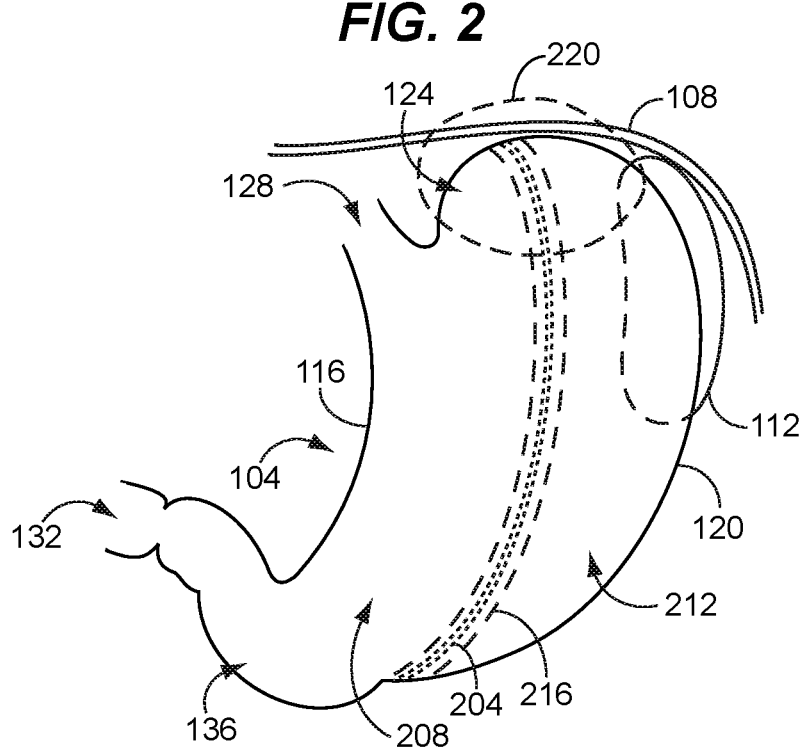
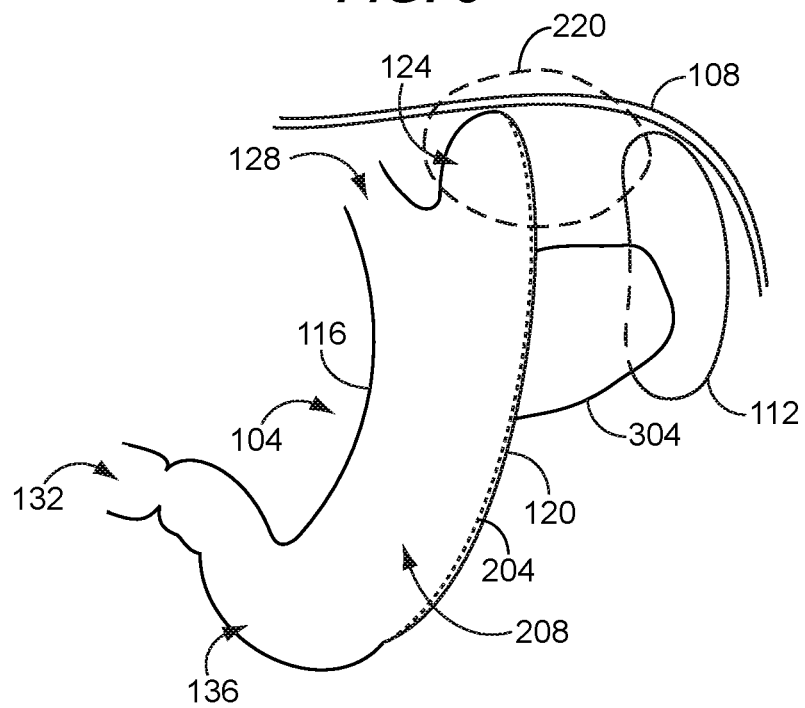

SAFE SLEEVE GASTRECTOMY

BACKGROUND OF THE INVENTION

Field of the Invention

The invention relates to bariatric treatments and in particular to a safe sleeve gastrectomy.

Related Art

Bariatric treatments may be used to treat obesity or other weight problems by reducing the size of a patient's stomach. The patient then consumes smaller portions of food leading to weight loss. Traditional bariatric treatments include gastric bypass surgery, gastric band surgery, gastric plication and placement of an intragastric balloon.

Sleeve gastrectomy is also a practiced bariatric treatment whereby the size of a patient's stomach is reduced to reduce appetite and induce weight loss. From the discussion that follows, it will become apparent that the present invention addresses the deficiencies associated with the prior art while providing numerous additional advantages and benefits not contemplated or possible with prior art constructions.

SUMMARY OF THE INVENTION

A safe sleeve gastrectomy is disclosed herein. As will be described further below, the safe sleeve gastrectomy improves upon the safety and provides a simplified process through which a gastrectomy can be achieved. The safe sleeve gastrectomy also reduces the risk of postoperative complications by reducing or eliminating mobilization, manipulation, dissection and division of organs and their connecting tissues. This also results in a significant reduction in the time required to perform a gastrectomy.

Various systems and methods for the safe sleeve gastrectomy are provided herein. For example, in one embodiment, a method for a safe sleeve gastrectomy comprises taking down a fundus of a stomach to create a safety pocket, creating an instrument tunnel at the posterior of the stomach with a first surgical instrument, and dividing the stomach into a pouch and a sectioned portion along the instrument tunnel with a second surgical instrument. The sectioned portion may be lifted with a grasping instrument, mobilized and removed.

The safety pocket may be located behind the fundus. In addition, the instrument tunnel may extend from a starting point at a pylorus of the stomach to an endpoint at the safety pocket. A bougie may also be inserted into the stomach to guide division of the stomach. For instance, at least a portion of the instrument tunnel may extend along the bougie. The instrument tunnel may be located at a posterior surface of the fundus. It is noted that the first surgical instrument may be an esophageal lifter while the second surgical instrument may be a stapler.

In another exemplary embodiment, a method for a safe sleeve gastrectomy comprises creating a safety pocket by moving a fundus of a patient's stomach downward, dividing a first portion of the stomach with a fusing instrument, and creating an instrument tunnel at a posterior side of the fundus with a surgical instrument. It is noted that the area around one or more short gastric vessels may be dissected to spread the apart the fundus and the patient's spleen.

This method also includes dividing a second portion of the stomach along the instrument tunnel with the fusing instrument. After the second portion is divided the stomach comprises a pouch and a sectioned portion. The sectioned portion of the stomach is mobilized and removed from the patient's body.

Similar to the above embodiment, the sectioned portion of the stomach may be lifted to provide visibility of a posterior side of the sectioned portion. A bougie may be inserted into the stomach, and if so, at least a portion of the instrument tunnel may extend along the bougie.

In addition, a portion of the fusing instrument may be inserted into the instrument tunnel when the second portion is divided. The fusing instrument may apply a plurality of rows of staples when dividing the first portion and the second portion of the stomach. Also, the instrument tunnel may extend from the division of the first portion of the stomach to an endpoint at the safety pocket.

In yet another exemplary embodiment, a method for a safe sleeve gastrectomy comprises creating a safety pocket by moving a fundus of a patient's stomach downward, creating an instrument tunnel at a posterior side of the fundus with a surgical instrument, dividing the stomach along the instrument tunnel with the fusing instrument, wherein after the stomach is divided the stomach comprises a pouch and a sectioned portion, mobilizing the sectioned portion of the stomach, and removing the sectioned portion from the patient's body.

It is noted that the area around one or more short gastric vessels may be dissected to spread the apart the fundus and the patient's spleen. It is contemplated that the short gastric vessels are not all divided during dissection of the area to improve safety to the patient during the safe sleeve gastrectomy.

The sectioned portion of the stomach may be lifted to provide visibility of a posterior side of the sectioned portion. A portion of the fusing instrument may be inserted into the instrument tunnel when the second portion is divided. In addition, the instrument tunnel may extend from a starting point at a pylorus of the stomach to an endpoint at the safety pocket. Also, a bougie may be inserted into the stomach to guide the division of the stomach. To illustrate, at least a portion of the instrument tunnel may extend along the bougie.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

FIG. 2 is an anterior view of an exemplary abdominal region of a patient having a divided stomach;

FIG. 3 is an anterior view of an exemplary abdominal region of a patient having a stomach with reduced gastric volume;

DETAILED DESCRIPTION OF THE INVENTION

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

Traditional sleeve gastrectomies are appealing for their effectiveness in inducing weight loss in patients. However, traditional sleeve gastrectomies involve extensive dissection and division of connective tissue, including blood vessels, at and around a patient's stomach to fully mobilize the stomach for division. For instance, the short gastric vessels from the spleen must be completely dissected and connective tissues between the stomach and diaphragm must be divided in traditional sleeve gastrectomies in order to fully mobilize the stomach. This divides and damages the blood supply at the top of the stomach, which increases the risk of postoperative leakage. In addition, extensively mobilizing the stomach is quite time consuming, and increases the risk of damage to the stomach as well as the short gastric vessels themselves.

With the safe sleeve gastrectomy herein, the blood supply to the remaining portion of the stomach, or pouch, is kept intact or almost entirely intact, decreasing postoperative complications. As will be described herein, the safe sleeve gastrectomy utilizes a safety pocket along natural tissue planes, simplifies and improves safety relative to traditional procedures, utilizes natural body structures (such as the epigastric fat pad) as guides for the procedure, and eliminates the need for elevation in suturing the gastric fundus which reduces the risk of leaks. In addition, since the stomach is not overly or fully mobilized, the safe sleeve gastrectomy can be completed in approximately a third of the time required for a traditional procedure.

Figure 1:
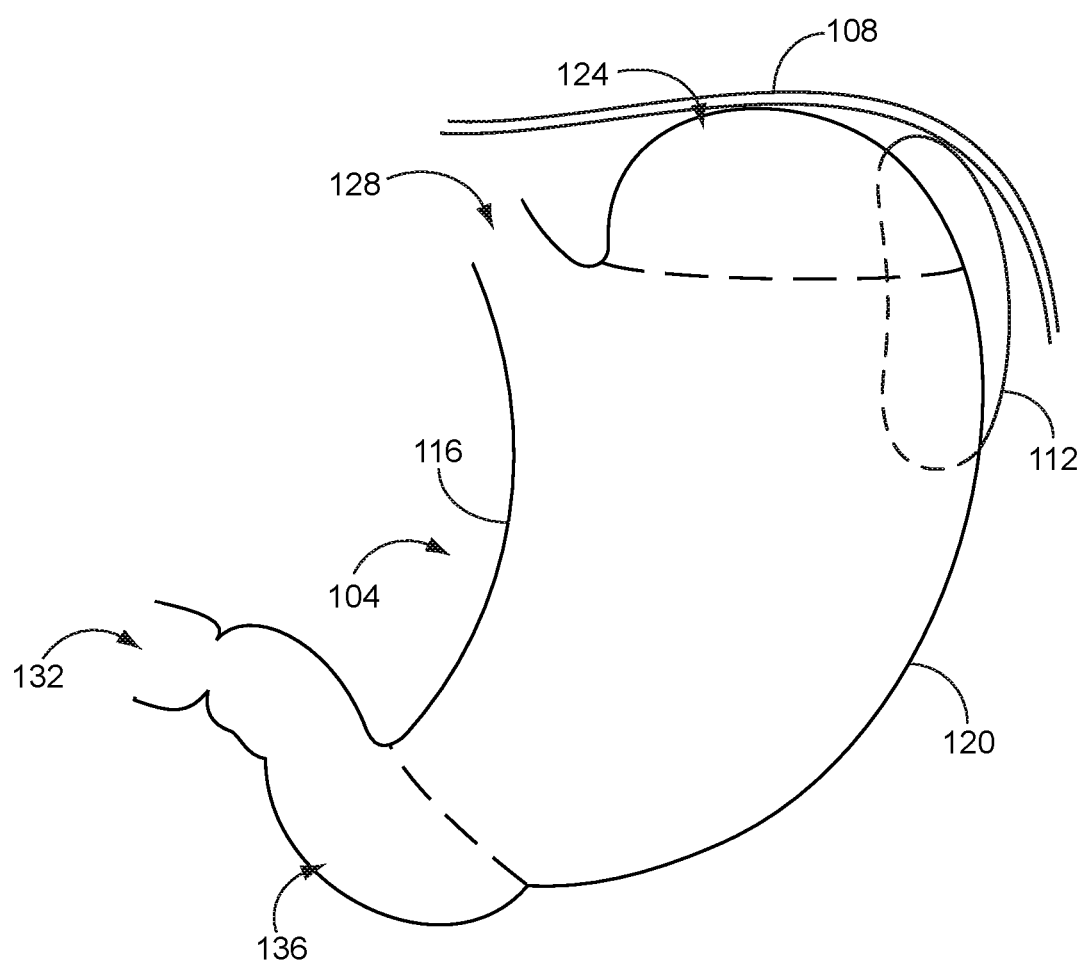
FIG. 1 is an anterior view of an exemplary abdominal region of a patient.

FIG. 1 illustrates an anterior view of an exemplary abdominal region of a patient. A stomach 104 and spleen 112 are illustrated. As can be seen, the stomach 104 has a lesser curve 116 and a greater curve 120 at is lateral areas. A fundus 124 is located at the stomach's top end, while a pylorus 136 is at the bottom end of the stomach 104. A cardial sphincter 128 connects the stomach 104 to the esophagus and allows ingested material to enter the stomach. After digestion, stomach contents pass through a pyloric sphincter 132 connects the stomach 104 to the small intestines.

A patient's spleen 112 will typically be located at or near the fundus 124 and may be at least partially behind the stomach 104. In addition, a patient's pancreas will typically be located behind the stomach 104 and may extend to be adjacent the spleen 112. Both the stomach 104 and spleen 112 will typically be positioned adjacent to a patient's diaphragm 108.

Generally speaking, the safe sleeve gastrectomy divides the stomach 104 via a laparoscopic surgical procedure, reducing its size and a patient's appetite to induce weight loss. FIGS. 2 and 3 illustrate a divided stomach 104 during and after the safe sleeve gastrectomy, respectively speaking.

As can be seen, a stomach 104 may be divided first by fusing or otherwise binding a length of the stomach 104 together to form a pouch 208 that forms a patient's new reduced size stomach, and a sectioned portion 212 that will be removed from the patient. As shown in FIG. 2 for example, the stomach 104 has been stapled with a plurality of staples 204 to form a pouch 208 and a sectioned portion. Though fusing is described with regard to a stapler, it will be understood that various other tissue fusing or binding instruments may be used.

In one or more embodiments, two or more rows of staples 204 may be applied (i.e., the stomach 104 may be fused along multiple parallel lines). This allows the stomach 104 to be cut therebetween, while containing and sealing the contents of the pouch 208 and the sectioned portion 212 of the stomach 104. The sectioned portion 212 may then be removed, leaving the pouch 208. As can be seen from FIG. 3, which illustrates the stomach 104 after a sectioned portion 212 thereof has been removed from the patient's body, the remaining pouch 208 has a reduced gastric volume.

During the safe sleeve gastrectomy, a safety pocket 220 is created, typically behind the spleen 112 and behind the stomach 104. A safety pocket 220 is advantageous in a number of ways. For instance, a safety pocket 220 creates room to accommodate surgical instruments, such as a stapler or an esophageal lifter, safely within the body. In addition, the safety pocket 220 is located in a naturally avascular area, which reduces the risk of vascular damage, such as by such surgical instruments.

Creation of a safety pocket 220 may also separate the spleen 112 from the stomach 104. This distances the fragile spleen 112 thereby reducing risk of damage to the same. Traditionally, all short gastric vessels between the stomach 104 and spleen 112 are divided and then the fundus 124 is completely mobilized. With a safety pocket 220, the area around the short gastric vessels need be dissected, if at all, to separate the stomach 104 and the spleen 112. If absolutely necessary, such as due to particular patient anatomy, the short gastric vessels may optionally be partially divided to achieve such separation. As can be seen, the blood supply is left untouched or largely intact.

During the safe sleeve gastrectomy, an instrument tunnel 216 or pathway is created beneath the stomach 104 at the posterior side of the stomach. To illustrate, with reference to FIG. 4A, a first surgical instrument such as an esophageal lifter 404 may be used to create an instrument tunnel 216 that extends from a starting point at or near the pylorus 136 to an endpoint at or near the fundus 124. As can be seen, a safety pocket 220 is located at the endpoint of the instrument tunnel 216. This allows a distal end of the esophageal lifter 404 to enter a safety pocket 220 to ensure the instrument tunnel 216 is completely excavated to accommodate a stapler along its entire length. It is noted that an instrument tunnel 216 need not extend this entire length, such as if there is good posterior access to one or more portions of the stomach. Typically, an instrument tunnel 216 will be required at least at the fundus 124 however.

Figure 4A:
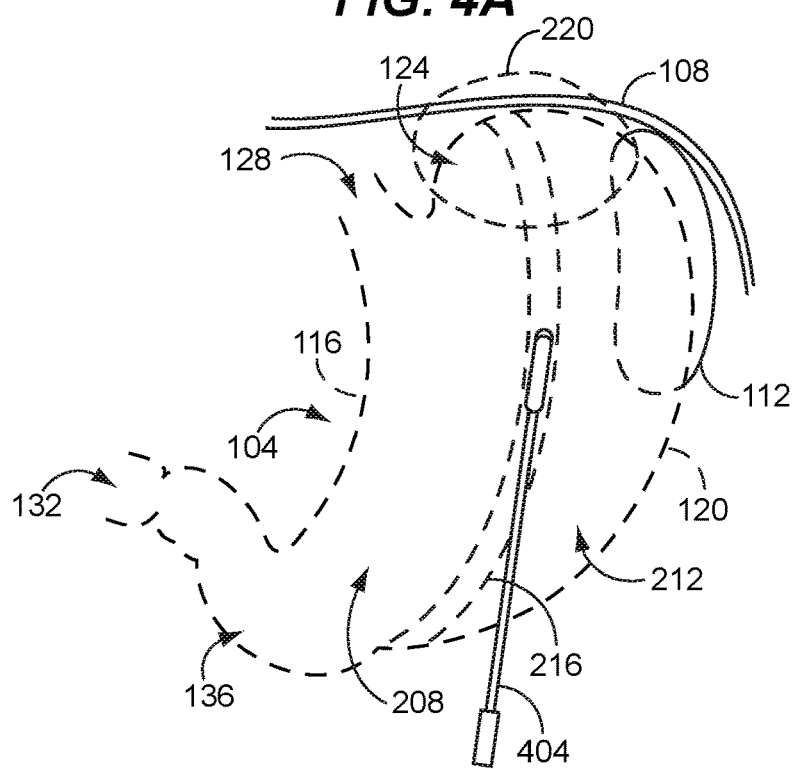
FIG. 4A is an anterior view of an exemplary abdominal region of a patient undergoing a safe sleeve gastrectomy.
Figure 4B:
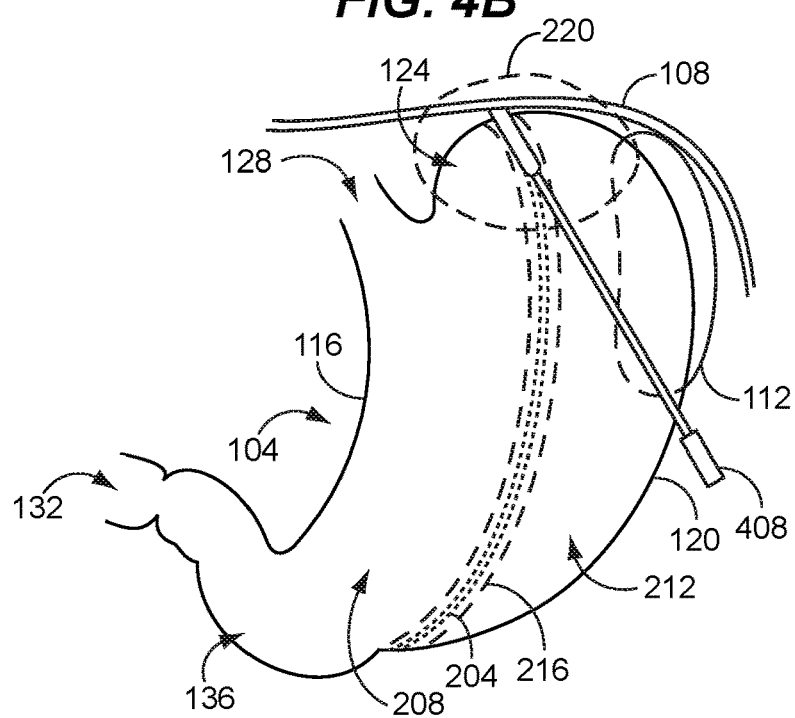
FIG. 4B is an anterior view of an exemplary abdominal region of a patient undergoing a safe sleeve gastrectomy.

Referring to FIG. 4B, staples 204 can be applied along the instrument tunnel 216 without overly or completely mobilizing the stomach 104. To illustrate, in FIG. 4A, a second surgical instrument, such as a stapler 408, applies staples 204 as it is advanced along the instrument tunnel 216. At the endpoint of the instrument tunnel 216, the distal end of the stapler 408 may extend into the safety pocket 220. This helps ensure that the stomach 104 is completely stapled, even to its edges, thereby preventing leakage.

Referring briefly back to FIG. 3, it can be seen that the stomach 104 is also adjacent the pancreas 304. Since the safe sleeve gastrectomy does not require extreme mobilization of the stomach 104 the procedure is typically safer for the pancreas 304 and other adjacent internal organs or body structures.

Figure 5:
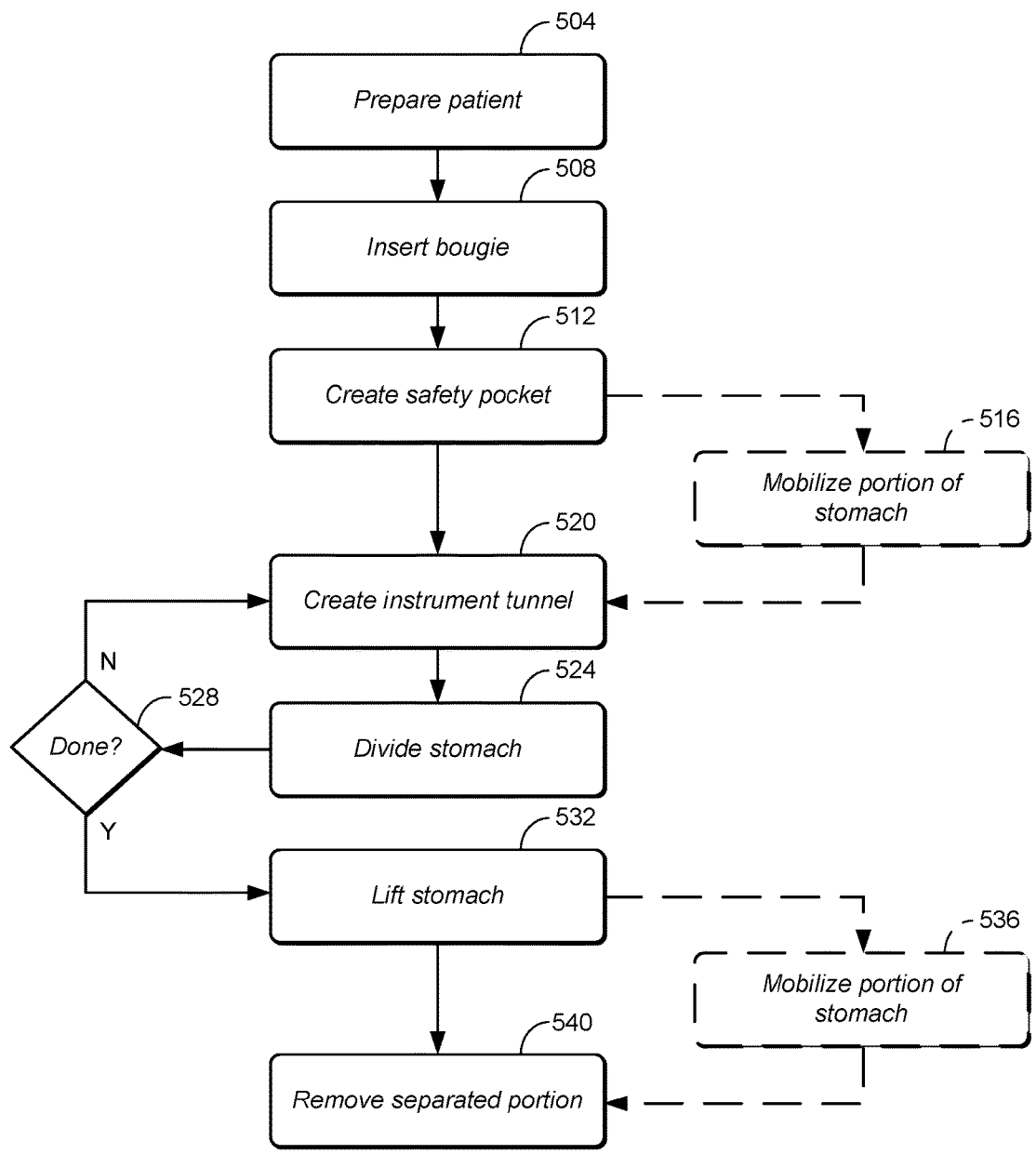
FIG. 5 is a flow diagram illustrating an exemplary procedure for a safe sleeve gastrectomy.

An exemplary safe sleeve gastrectomy will now be described with regard to FIG. 5 and with reference to FIGS. 4A and 4B. FIG. 5 is a flow diagram illustrating an exemplary procedure to conduct the safe sleeve gastrectomy. Though shown in a particular sequence, it is contemplated that the various steps herein may be performed in different sequences.

At a step 504, a patient is prepared for the safe sleeve gastrectomy. Any sterilization, anesthesia, draping and other patient preparation may occur at this step. At a step 508, a bougie, tube or the like may be inserted into the patient's stomach 104. As will be described further below, a bougie may be used as a guide for diving the stomach during the safe sleeve gastrectomy.

At a step 512, a safety pocket 220 may be created. As described above, a safety pocket 220 may be created by taking down a top portion or fundus 124 of the stomach. This creates a void near the stomach 104 and spleen 112 for further use during the safe sleeve gastrectomy. In typical patient anatomy, the safety pocket 220 will be behind the stomach 104 and spleen 112.

It is noted that a portion of the stomach 104 may optionally be mobilized at a step 516. For instance, the stomach 104 may be mobilized along its greater curve 120 in some embodiments. This mobilization can be helpful in creating an instrument tunnel, dividing the stomach 104 or both by providing visibility and access to a portion of the posterior side of the stomach 104. One or more surgical instruments will typically be utilized during mobilization. Some exemplary mobilization instruments include scissors, cutters, sealers (such as a COVIDIEN LIGASURE) and scalpels. As will be described below, the mobilization of optional step 516 may occur after the stomach has been divided.

At a step 520, an instrument tunnel 216 may be created. The path of an instrument tunnel 216 may be determined by a surgeon such as to achieve a desired reduction of the stomach 104. A bougie may be inserted into the stomach 104 to provide a structure that guides the path of an instrument tunnel 216. As stated above, the endpoint of the instrument tunnel may be at the safety pocket 220. In one or more embodiments, a surgeon may choose a path for an instrument tunnel 216 that ends at or near an epigastric fat pad at the safety pocket 220. Since the safety pocket 220 (and epigastric fat pad thereof) is at an avascular area, a surgeon can operate their surgical instruments in this area with reduced risk.

An instrument tunnel may be created with a variety of surgical instruments. In one or more embodiments, an esophageal lifter or graspers are used to create the instrument tunnel such as by separating avascular tissues along the posterior of the stomach as the instrument is advanced along a selected path.

At a step 524, the stomach may be divided by fusing the stomach 104 together along the path of the instrument tunnel 216 to create a pouch 208 and a sectioned portion 212 of the stomach, such as described above. In one or more embodiments this may occur by advancing a stapler 408 along the instrument tunnel 216 and applying staples 204 as the stapler is advanced from a starting point to an endpoint of the instrument tunnel 216.

As will be described further below, a stapler 408 will typically have an upper jaw and a lower jaw, with the lower jaw being advanced in the instrument tunnel 216 along the posterior of the stomach 104 while the upper jaw is advanced along the anterior of the stomach. Staples 204 can then be applied by closing or otherwise manipulating the upper and lower jaws to fuse the stomach along the path of the instrument tunnel 216.

An instrument tunnel 216 and division of the stomach 104 may occur on a section by section basis. At a decision step 528, if division of the stomach 104 is incomplete, additional sections of the instrument tunnel 216 may be created at step 520. Thereafter, the newly created section can be divided, such as by fusing the section at step 524 with a stapler 408 or other fusing instrument, as described above.

In one or more embodiments, a fusing instrument, such as a stapler 408 as described above, may also cut the stomach 104 as it is fusing the stomach together along the instrument tunnel 216. As described above, multiple rows of staples 204 may be applied to seal the pouch 208 and the sectioned portion 212. The stomach 104 can therefore be cut between such fused rows or lines to divide the pouch 208 from the sectioned portion 212. As will be described below with regard to optional step 528, it is contemplated that a cutting instrument, such as scissors may alternatively be used to cut the stomach 104, such as in extremely rare cases where the fusing instrument does not perform a cutting operation.

If division of the stomach 104 is complete at decision step 528, the safe sleeve gastrectomy may continue by lifting the sectioned portion 212 of the stomach at a step 532. The stomach 104 may be lifted to permit the sectioned portion 212 thereof to be inspected, mobilized or both. Lifting the stomach 104 provides access to the posterior of the stomach as well as good visualization of the same. If necessary, at an optional step 536, connecting tissues, including blood vessels, may then be divided from the sectioned portion 212 with increased visibility to mobilize the sectioned portion 212. For example, if not previously mobilized, such as at step 516, the greater curve 120 and other areas of the sectioned portion may be mobilized at step 536.

Once the sectioned portion 212 is completely mobilized, the sectioned portion may be removed from the patient at a step 540. Thereafter the safe sleeve gastrectomy may be considered complete.

Figure 6A:
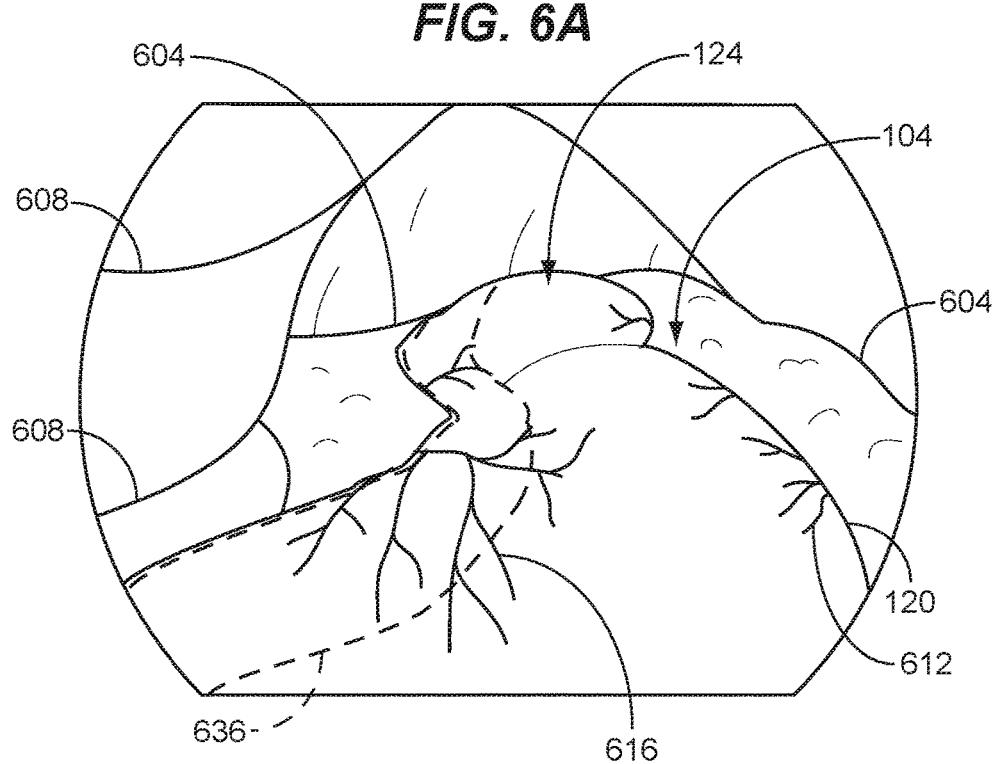
FIG. 6A is an anterior perspective view of an exemplary abdominal region of a patient.

FIGS. 6A-6F illustrate an exemplary safe sleeve gastrectomy from the perspective of a laparoscope. FIG. 6A illustrates an exemplary abdominal region of a patient, including a view of the patient's stomach 104 and surrounding fatty and other connecting tissue 604. The liver 608 has been elevated out of the way to provide access to and visibility of the stomach 104 and surrounding areas. As described above, a bougie 636 may routinely be inserted into the stomach 104 to function as a guide for dividing the stomach. In other words, the stomach 104 may be divided along the periphery of the bougie 636.

Figure 6B:
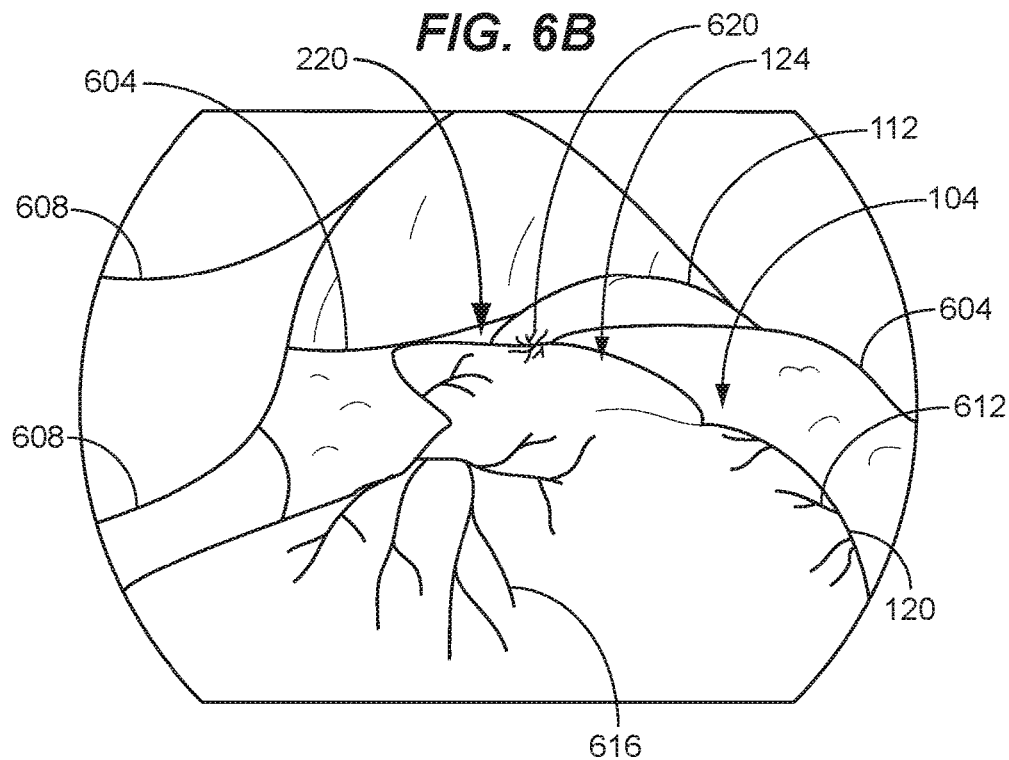
FIG. 6B is an anterior perspective view of an exemplary abdominal region of a patient undergoing safety pocket creation.

In FIG. 6B, the fundus 124 has been taken down by moving it downward. It is contemplated that a grasper or other surgical instrument may be used to manipulate the fundus 124 in this manner. Taking the fundus 124 down mobilizes and exposes the spleen 112 and creates a safety pocket 220, such as described above. It is noted that, if the fundus 124 is adhered, any connecting tissue may be dissected or divided to mobilize the fundus sufficient to take it down.

Typically, short gastric vessels 620 would divided but the blood supply to the fundus 124 would be left intact during the safe sleeve gastrectomy. Again, this is in contrast to traditional procedures where the entire stomach 104 and funds 124 would be mobilized all at once, cutting the blood supply and risking damage to the stomach 104 and surrounding organs, which is especially dangerous near the spleen 112 where dissection or division of the short gastric vessels 620 exposes largerblood vessels deep within the body. If necessary, a portion of the short gastric vessels 620 may be dissected or divided only to the extent necessary to allow the fundus 124 to be moved downward and away from the spleen 112 (i.e., taken down). This preserves the blood supply between the fundus 124.

Figure 6C:
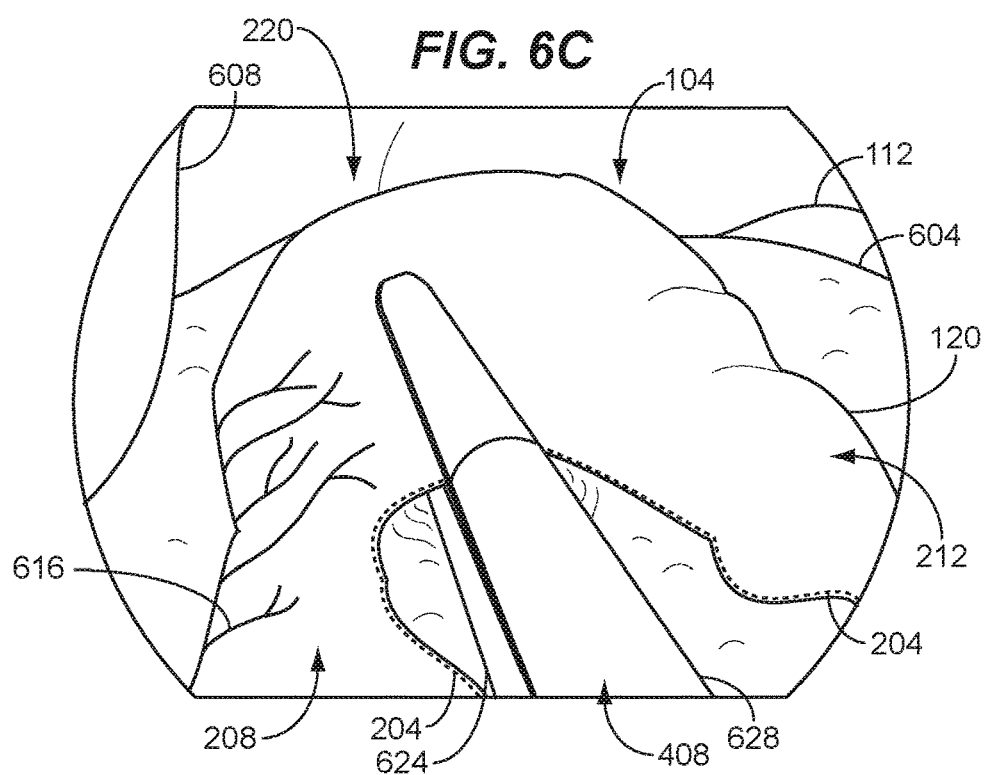
FIG. 6C is an anterior perspective view of an exemplary stomach undergoing division.
Figure 6D:
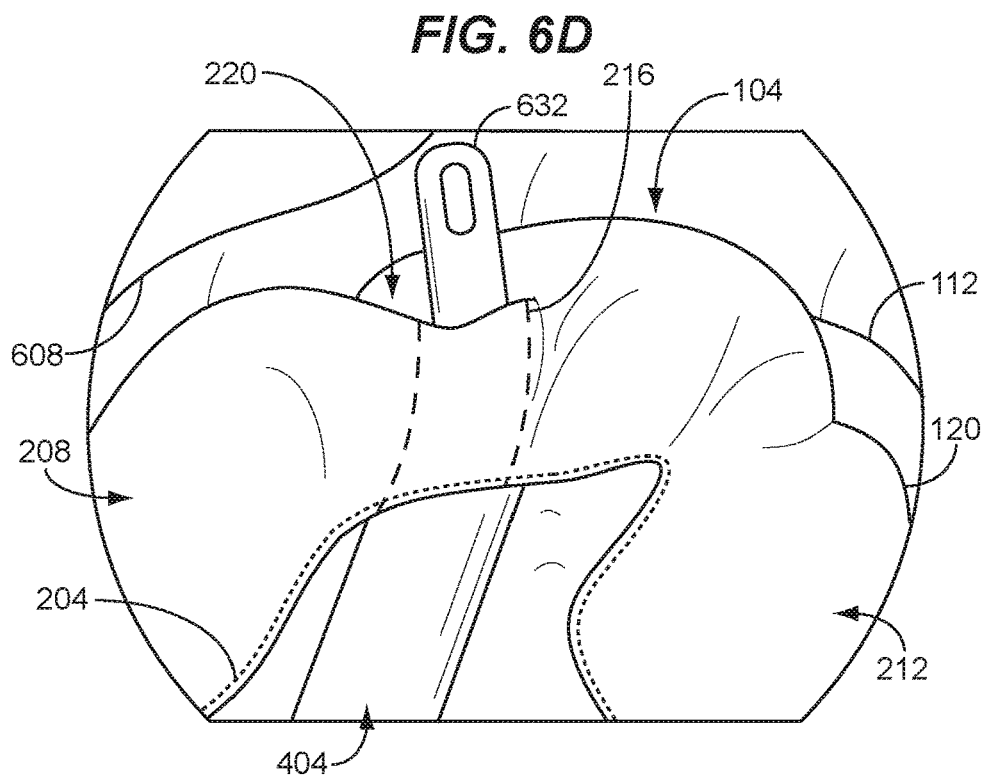
FIG. 6D is an anterior perspective view of an exemplary stomach undergoing instrument tunneling.

FIGS. 6C and 6D illustrate an exemplary incremental process by which a stomach 104 may be divided through an instrument tunnel 216. As can be seen, a fusing instrument, such as a stapler 408, may be advanced along the stomach 104 to divide the stomach. A stapler 408 may comprise a lower jaw 624 and an upper jaw 628 which are closed together to apply staples 204. A stapler 408 may also divide or cut the stomach 104 between individual rows of staples 204, as described above. Therefore, it is advantageous to have a space at the posterior surface of the stomach 104 to accommodate the lower jaw 624 and upper jaw 628.

It is noted that portions of a stomach 104 may already be sufficiently mobile to allow the stapler 408 to operate safely and unhindered. For example, one or more portions of a stomach 104 may sufficiently mobile to move the same into the lower jaw 624 and upper jaw 628 for stapling. Typically however, this will not be the case for the entire stomach 104.

An instrument tunnel 216 may therefore be created along at least some of the posterior of the stomach 104 to accommodate a stapler 408. As shown in FIG. 6B, an instrument tunnel 216 may be created by a surgical instrument, such as an esophageal lifter 404 or graspers, which separates connecting tissues to create the instrument tunnel. An esophageal lifter 404 may have an appendage 632 at its distal end that is pivotable or otherwise movable to separate connecting tissues.

Figure 6E:
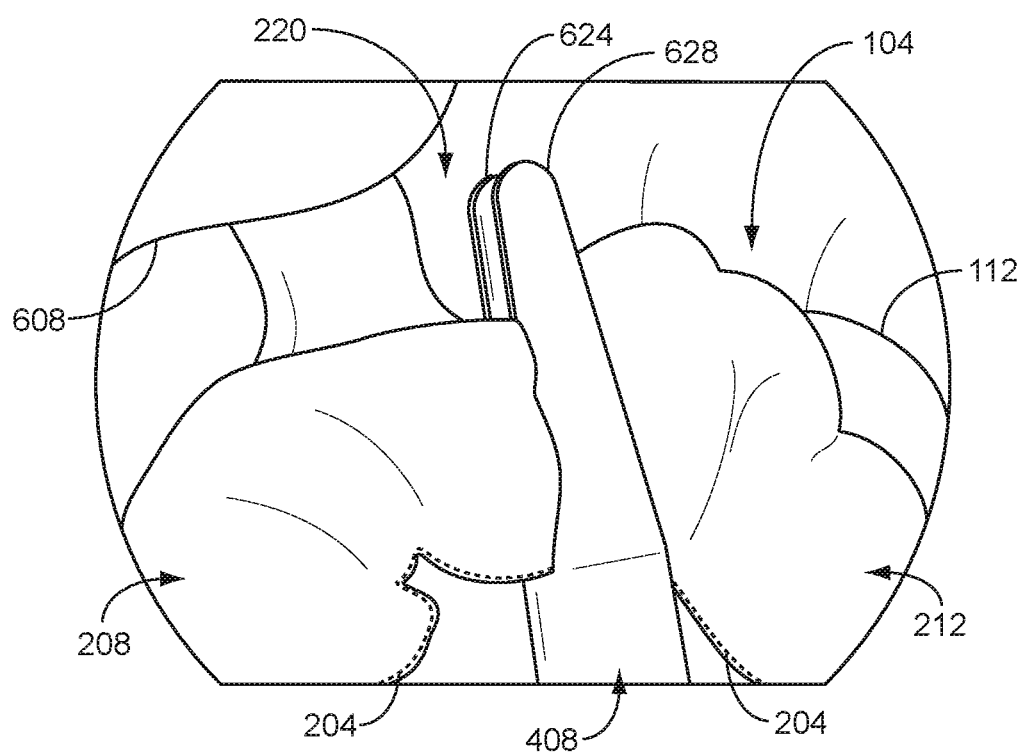
FIG. 6E is an anterior perspective view of an exemplary stomach undergoing division.

FIG. 6E illustrates a stapler 408 utilizing the instrument tunnel 216 created by the esophageal lifter 408 to complete stapling of the stomach 104. As can be seen, a lower jaw 624 of the stapler 408 enters the instrument tunnel 216 to engage the posterior of the stomach 104. Thereafter the lower jaw 624 and upper jaw 628 can be closed to apply staples 204 along their length.

FIGS. 6D and 6E also illustrate the benefit of a safety pocket 220. As can be seen in FIG. 6D, the esophageal lifter 404 can safely extend beyond the edge of the stomach 104 and into the safety pocket 220 to ensure that an instrument tunnel 216 extends all the way to its endpoint. As shown in FIG. 6E, a stapler 408 can extend beyond the edge of a stomach 104 and into the safety pocket 220 to ensure that the staples 204 extend all the way to the edge of the stomach to fully fuse the stomach and prevent leakage. This is especially advantageous in cases where a fusing instrument, such as a stapler 408, does not fuse or staple all the way to its distal end.

Figure 6F:
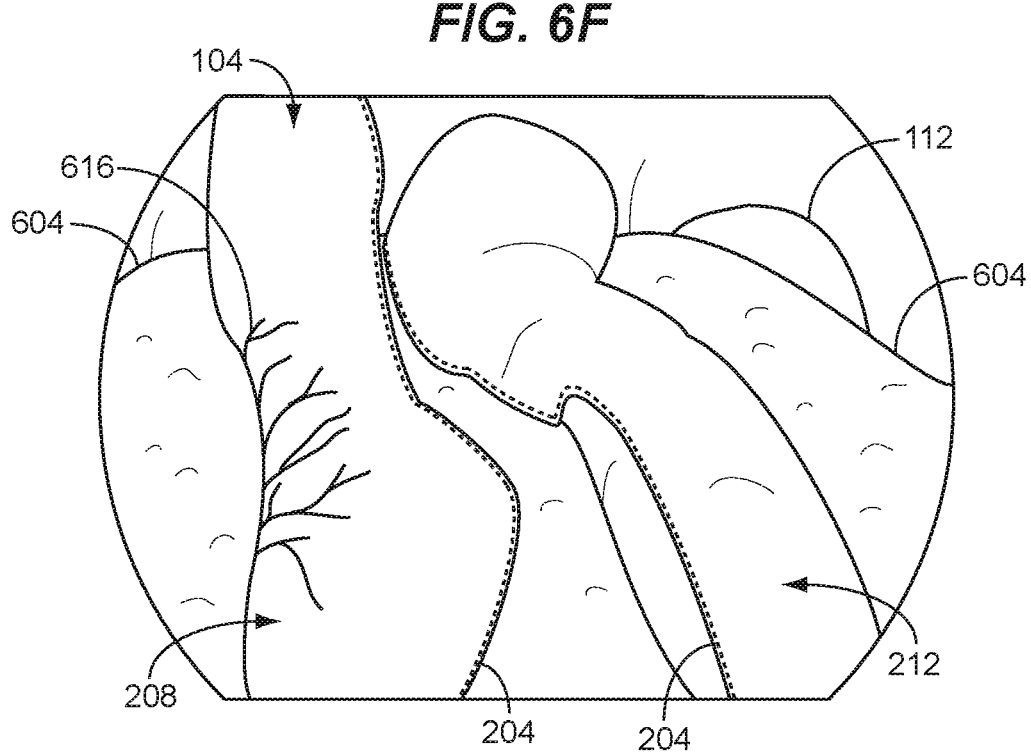
FIG. 6F is an anterior perspective view of an exemplary stomach after division.

FIG. 6F illustrates a completely divided stomach 104. As can be seen, the pouch 208 and sectioned portion 212 are completely separated. Also, the pouch 208 and sectioned portion 212 are both sealed to prevent leakage. The pouch 208 remains connected to the blood supply by blood vessels 616.

Figure 6G:
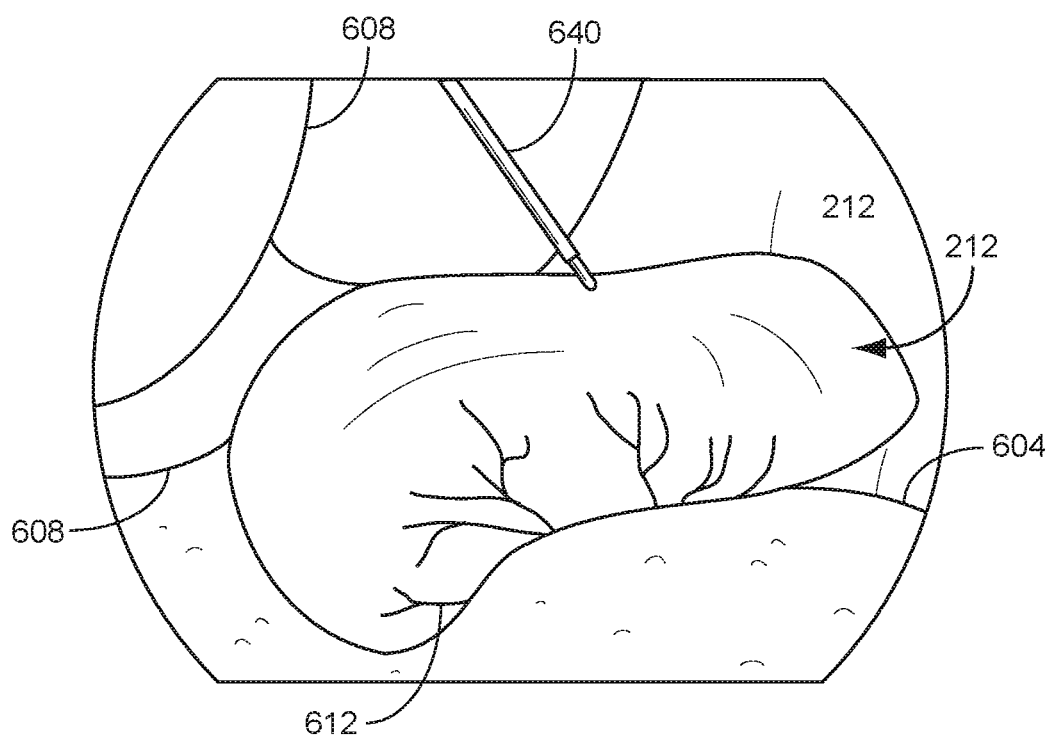
FIG. 6G is a posterior perspective view of an exemplary sectioned portion after division.

The sectioned portion 212 can then be completely mobilized to allow removal thereof from the patient's body. As shown in FIG. 6G, the sectioned portion 212 can be lifted, such as by a grasper 640, to divide any connecting tissue or blood vessels 612 to allow removal of the sectioned portion 212 at the posterior of the sectioned portion. Lifting provides greatly increased visibility and safety at the posterior of the section portion 212. The section portion 212 can then be removed from the patient's body, leaving the pouch 208 as a stomach 104 of reduced size.

The safe sleeve gastrectomy also utilizes a "no touch" methodology whereby pulling, grasping or even touching a patient's organs is limited. In contrast to traditional procedures, where the stomach is overly mobilized and pulled and grasped while doing so, the safe sleeve gastrectomy limits grasping and pulling to the remaining sectioned portion of the stomach. The sectioned portion will be removed from the patient and therefore complications caused by grasping or pulling are eliminated or greatly reduced. If manipulation of the pouch is desired, such as due to a particular patient's anatomy, a surgeon may do so by grasping the pouch at the staples, where the risk of damage is low. Otherwise, the pouch is left in place and does not need to be grasped or pulled (but may be moved) during the safe sleeve gastrectomy.

While various embodiments of the invention have been described, it will be apparent to those of ordinary skill in the art that many more embodiments and implementations are possible that are within the scope of this invention. In addition, the various features, elements, and embodiments described herein may be claimed or combined in any combination or arrangement.

What is claimed is:

1. A method for a safe sleeve gastrectomy comprising:
creating a safety pocket by taking down a fundus of a stomach;
creating an instrument tunnel at a posterior of the stomach with a first surgical instrument;
dividing the stomach into a pouch and a sectioned portion along the instrument tunnel with a second surgical instrument;
lifting the sectioned portion with a grasping instrument;
mobilizing the sectioned portion; and
removing the sectioned portion.

2. The method of claim 1, wherein the safety pocket is behind the fundus.

3. The method of claim 1, wherein the instrument tunnel extends from a starting point at a pylorus of the stomach to an endpoint at the safety pocket.

4. The method of claim 1, further comprising inserting a bougie into the stomach, wherein at least a portion of the instrument tunnel extends along the bougie.

5. The method of claim 1, wherein the instrument tunnel is located at a posterior surface of the fundus.

6. The method of claim 1, wherein the first surgical instrument is an esophageal lifter.

7. The method of claim 1, wherein the second surgical instrument is a stapler.

8. A method for a safe sleeve gastrectomy comprising:
creating a safety pocket by moving a fundus of a patient's stomach downward;
dividing a first portion of the stomach with a fusing instrument;

creating an instrument tunnel at a posterior side of the fundus with a surgical instrument;

dividing a second portion of the stomach along the instrument tunnel with the fusing instrument, wherein after the second portion is divided the stomach comprises a pouch and a sectioned portion;

mobilizing the sectioned portion of the stomach; and removing the sectioned portion from the patient's body.

9. The method of claim 8, further comprising lifting the sectioned portion of the stomach to provide visibility of a posterior side of the sectioned portion.

10. The method of claim 8, wherein a portion of the fusing instrument is inserted into the instrument tunnel when the second portion is divided.

11. The method of claim 8, wherein the instrument tunnel extends from the division of the first portion of the stomach to an endpoint at the safety pocket.

12. The method of claim 8, further comprising inserting a bougie into the stomach, wherein at least a portion of the instrument tunnel extends along the bougie.

13. The method of claim 8, wherein the fusing instrument applies a plurality of rows of staples when dividing the first portion and the second portion of the stomach.

14. The method of claim 8, further comprising dissecting the area around one or more short gastric vessels to spread apart the fundus and the patient's spleen.

15. A method for a safe sleeve gastrectomy comprising:
creating a safety pocket by moving a fundus of a patient's stomach downward;

creating an instrument tunnel at a posterior side of the fundus with a surgical instrument;

dividing the stomach along the instrument tunnel with a fusing instrument, wherein after the stomach is divided the stomach comprises a pouch and a sectioned portion;

mobilizing the sectioned portion of the stomach; and removing the sectioned portion from the patient's body.

16. The method of claim 15 further comprising lifting the sectioned portion of the stomach to provide visibility of a posterior side of the sectioned portion.

17. The method of claim 15, wherein a portion of the fusing instrument is inserted into the instrument tunnel when the stomach is divided.

18. The method of claim 15, wherein the instrument tunnel extends from a starting point at a pylorus of the stomach to an endpoint at the safety pocket.

19. The method of claim 15 further comprising inserting a bougie into the stomach, wherein at least a portion of the instrument tunnel extends along the bougie.

20. The method of claim 15 further comprising dissecting the area around one or more short gastric vessels to spread the apart the fundus and the patient's spleen, wherein the one or more short gastric vessels are not divided during dissection of the area.

* * * * *